(12) United States Patent
Park

(10) Patent No.: US 7,585,525 B2
(45) Date of Patent: Sep. 8, 2009

(54) METHOD FOR PROCESSING GINSENG AND THE USES OF EXTRACT OF PROCESSED GINSENG

(75) Inventor: Myung Hwan Park, Seoul (KR)

(73) Assignee: Lotte Confectionery Co., Ltd., Seoul (KR)

( * ) Notice: Subject to any disclaimer, the term of this patent is extended or adjusted under 35 U.S.C. 154(b) by 442 days.

(21) Appl. No.: 10/482,782

(22) PCT Filed: Jan. 2, 2003

(86) PCT No.: PCT/KR03/00003

§ 371 (c)(1),
(2), (4) Date: Aug. 24, 2004

(87) PCT Pub. No.: WO03/056929

PCT Pub. Date: Jul. 17, 2003

(65) Prior Publication Data

US 2005/0031711 A1      Feb. 10, 2005

(30) Foreign Application Priority Data

Jan. 5, 2002    (KR) ...................... 10-2002-0000572

(51) Int. Cl.
*A61K 35/25* (2006.01)
*A61K 36/00* (2006.01)

(52) U.S. Cl. ...................... 424/728; 424/725

(58) Field of Classification Search .................. None
See application file for complete search history.

(56) References Cited

U.S. PATENT DOCUMENTS 5,776,460 A * 7/1998 Kim et al. .................. 424/728

6,083,932 A    7/2000 Pang et al.

FOREIGN PATENT DOCUMENTS

| JP | 61194031 A | * | 8/1986 |
| JP | 361194031 A | * | 8/1986 |
| JP | 05009123 A | * | 1/1993 |
| KR | 97-58578 | | 8/1997 |
| KR | 99-458 | | 1/1999 |
| KR | 185539 | * | 5/1999 |
| KR | 2002008726 A | * | 1/2002 |

OTHER PUBLICATIONS

Phillipson, J. New Drugs From Nature—It Could Be Yew; Phytotherapy Research 13 (1999) pp. 2-8.*
Revilla et al. Comparison of Several Procedures Used for the Extraction of Anthocyanins From Red Grapes; J. Agric. Food Chem. 1998, 46, pp. 4592-4597.*
Duke, J. Chemicals in: Panax Quinquefolis L. (Araliaceae)—American Ginseng, Ginseng; Dr. duke's Phytochemical and Ethnobotanical Databases: URL<http://www.ars-grin.gov/cgi-bin/duke/farmacy2.pl> pp. 1-9.*

* cited by examiner

*Primary Examiner*—Patricia Leith
(74) *Attorney, Agent, or Firm*—William E. Beaumont

(57) ABSTRACT

The present invention relates to a method of processing ginseng and the uses of the extract of processed ginseng. More particularly, the present invention relates to extract of the processed ginseng which can improve the ratio of ginsenoside (Rg3+Rg5)/(Rb1+Rb2+Rc+Rd) to 10-45 due to a synergy effect by mixing ginseng with herbal drugs such as Schizandrae Fructus, Crataegi Fructus, Corni Fructus, Chaenomelis Fructus, Mume Fructus, Citrus junos, Aurantii Fructus, apples, Fructus of *Punica granatum* and *Citrus limon*, extract of saponin fraction of the processed ginseng, and a method of processing ginseng via heat treatment of the mixture of ingredients comprising the mixture of ingredients comprising ginseng and the aforementioned herbal drug(s) at a temperature of 70-120° C.

6 Claims, 3 Drawing Sheets

US 7,585,525 B2

METHOD FOR PROCESSING GINSENG AND THE USES OF EXTRACT OF PROCESSED GINSENG

TECHNICAL FIELD

The present invention relates to a method for processing ginseng and the uses of the extract of the processed ginseng. More particularly, the present invention relates to extract of processed ginseng or extract of saponin fraction of the processed ginseng, which improves the ratio of ginsenoside (Rg3+Rg5)/(Rb1+Rb2+Rc+Rd) to 10-45 due to a synergic effect by mixing ginseng with one of the following herbal drugs such as Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon, and a method for processing ginseng by heating the mixture of ingredients at a temperature of 70-120° C. comprising ginseng and the aforementioned herbal drugs.

BACKGROUND ART

Ginseng is a globally well-known nourishing tonic. Therefore, extensive studies have been carried out to identify and characterize its constituents as well as its pharmacological actions of the constitutents. These studies have revealed that the ginseng has a variety of thereapeutic effects such as preventing aging process and arteriosclerosis; improving hyperlipemia, diabetes, hypertension, cerebral functions and hepatic functions; antioxidation; antistress; strengthening immune responses; improving antithrombotic effect; protecting cerebral neurons; anticancer effects, etc. Recently, it was reported that red ginseng contains a little amount of Rg3, a ginsenoside having various effects such as relaxation of blood vessels [J. Nat. Prod. 63, 1702(2000)], inhibition of platelet aggregations [Biol. Pharm. Bull. 21, 79(1998), Korean J. Ginseng Sci. 21, 132(1997)], protection of cerebral neurons [J. Neuroscience Res. 53, 426(1998), Neuro Report 9, 226 (1998)], while ginsenosides Rg3, Rg5, Rh2, and Rh1 have anticancer activities [Jpn. J. cancer Res. 87, 357(1996), J. cancer Res. Clin. Oncol. 120, 24(1993), Anticancer Res. 17, 1067(1997), Cancer Letters 150, 41(2000), Dietary Anticarcinogenesis and Antimutagenesis 274(2000)].

Fresh ginseng has been customarily processed into white ginseng or red ginseng for long-term storage purpose. It has been also reported that red ginseng, contains trace amount of ginsenosides such as Rg3, Rg5, Rh1, Rh2, and Rh1 as well as maltol not contained in fresh ginseng or white ginseng, thus imparting improved therapeutic effects. There has been also invented an equipment which can prepare red ginseng extract from fresh ginseng or white ginseng (Korea Unexamined Patent Publication No. 10-2001-19628). Additionally, there have been also studies mainly focused on improving pharmaceutical effects by fortifying the aforementioned ginsenosides contained in small amounts in red ginseng.

Recently it was revealed that 'sun ginseng', a type of ginseng processed via a novel method, wherein ginseng is heat-treated at a temperature of 120-180° C., a temperature much higher than that used in manufacturing red ginseng, thereby increasing the contents of the pharmaceutically important constituents usually contained in small amounts in conventional red ginseng and also producing new components, can improve existing pharmaceutical effects [J. Natural Products 63, 1702, 2000, Korea Patent No. 192678]. However, this method has a few drawbacks that it requires special equipments such as a high-pressure heater and it also requires a high heat treatment at a temperature higher than those used conventionally thus resulting in carbonization of ginseng, especially in the case of mass production.

SUMMARY OF THE INVENTION

Accordingly, an object of the present invention is to provide a novel method for processing ginseng wherein the extract of processed ginseng can have remarkably fortified ginsenoside contents with much improved pharmaceutical effects. In the present invention, the inventors admixed ginseng and other pharmaceutically important herbal drugs and heated the mixture at a temperature of 70-120° C. and finally obtained the processed ginseng extract wherein the ratio of ginsenoside (Rg3+Rg5)/(Rb1+Rb2+Rc+Rd) is improved to 10-45, preferably 20-45, thereby drastically increasing the pharmaceutical effects of the processed ginseng extract. For example, thus obtained extract of the processed ginseng prepared according to the present invention has shown that the relaxation rate of blood vessels is increased about 65-97 times compared to those of conventional ginseng. Further, in the present invention, ginseng is mixed with at least one herbal drugs selected from the group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon, and heat-treated at a temperature of 70-120° C., which results in conversion of protopanaxadiol-based saponins into ginsenosides such as Rg3, Rg5, Rk1 while protopanaxatriol-based saponins are converted into ginsenosides such as Rg2, F4, Rh1 and the like.

Another object of the present invention is to provide extract of saponin fraction of the processed ginseng and extract of saponin fraction of the processed ginseng wherein the ratio of ginsenoside (Rg3+Rg5)/(Rb1+Rb2+Rc+Rd) is 10-45, preferably 20-45, with much improved pharmaceutical effects.

Still another object of the present invention is to provide supplementary health drinks comprising concentrated or diluted extract of the processed ginseng aforementioned.

Still another object of the present invention is to provide supplementary health foods or pharmaceutical drugs in the form of tablets, capsules, pills, granules, etc., comprising the extract of processed ginseng aforementioned.

BRIEF DESCRIPTION OF DRAWINGS

The aforementioned aspects and other features of the present invention will be explained in the following description, taken in conjunction with the accompanying drawings, wherein.

DISCLOSURE OF INVENTION

Figure 1:
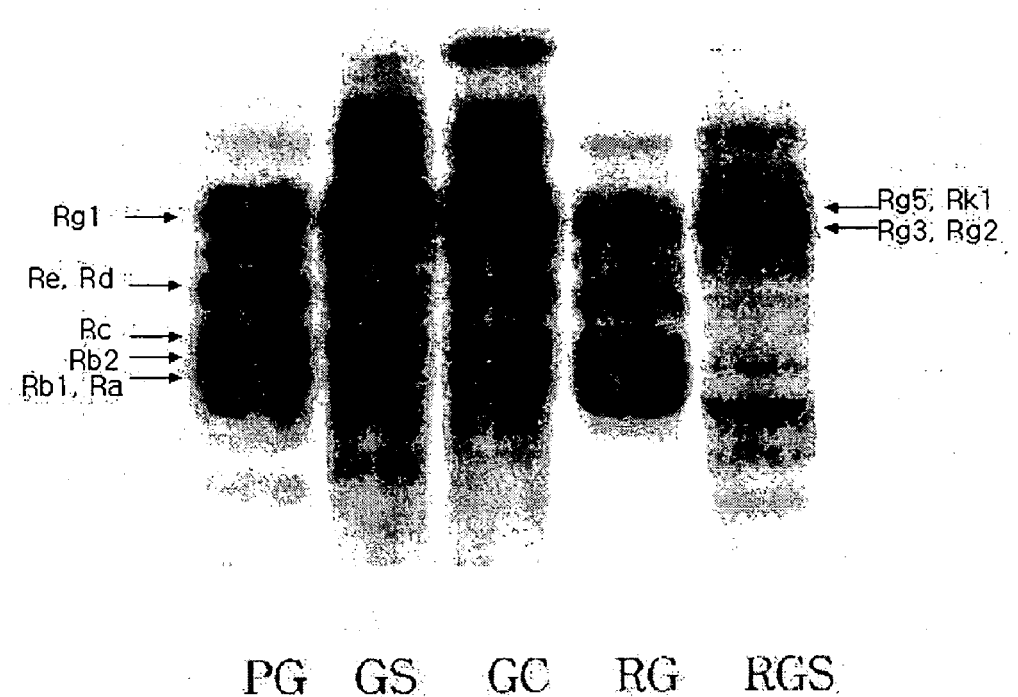
FIG. 1 shows a thin layer chromatogram of saponin fraction of the processed ginseng of the present invention and saponin fraction of the conventional ginseng (PG: Comp. Ex. 4; GC: Ex. 21; GS: Ex. 22; RG: Comp. Ex. 5; RGS: Ex. 28)

The present invention relates to the extract of processed ginseng or its saponin fraction extract wherein the ratio of ginsenoside (Rg3+Rg5)/(Rb1+Rb2+Rc+Rd) is 10-45.

The present invention also relates to a novel method for processing ginseng wherein ginseng is admixed with at least one herbal drug selected from the group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon, and the mixture is processed under heat treatment at a temperature of 70-120° C.

The present invention also relates to a pharmaceutical drug or a health food prepared in a variety of forms comprising the aforementioned extract of the processed ginseng or its saponin fraction extract as an active ingredient based on the result that the extract of the processed ginseng or its saponin fraction extract are effective in treatment as well as prevention of cardiovascular diseases, erectile dysfunction, cerebral neurons and the related diseases, anticancer, etc.

The present invention is described in more detail as set forth hereunder.

In the present invention, with reference to 100 parts of ginseng used the amount of acidic natured herbal drugs used is 10-1000 parts with reference to at least one selected from the group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon. The selected herbal drug(s) and ginseng are admixed and heated for 1-6 hr in the presence of 4-10 times weight of water with reference to the weight of the above mixture, cooled down to a room temperature, filtrated, concentrated and finally prepared into a form of extract or powder. More specifically, the amount of water used in this step is 7-10 times greater than that of the above mixture at the initial stage of extraction.

The heating process is performed at a temperature of 70-120° C., preferably at a boiling temperature of the ingredients. In addition, the use of a conventional equipment for industrial use is sufficient for commercial mass production without further necessitating sophisticated equipments.

The period of time required for heating process is 1-6 hours, preferably 3-5 hours. If the heating process is performed for longer than 6 hours it is likely that ginsenosides Rg3 and Rg5 may be decomposed while there will be no apparent change in the total yield of the extract.

Thus obtained extract of the processed ginseng can be directly used to meet the objective of the present invention, however, the extraction may further comprise steps of evaporation of water followed by heat extraction for 1-3 hours in the presence of ethanol or methanol. The introduction of the alcohol extraction process will enable to obtain a more desirable result, especially when it is applied to a process designed for improving extraction yield of saponins.

Thus obtained extract of the processed ginseng generally contains pharmaceutically non-effective impurities originated from the herbal drugs and ginseng. Therefore, thus obtained extract of the processed ginseng can be further purified by using steps, comprising:

extracting by using dichloromethane;

extracting the aqueous phase of the above extract a few times by using water-saturated butanol and combining the butanol extracts;

washing the butanol extract with water;

concentrating of the above butanol extract; and dissolving the above concentrated butanol extract in methanol.

The above process can increase the purity of the targeted saponin fraction extract and this purified saponin fraction extract can be used in manufacturing products requiring higher purity of saponins.

Examples of the ginsengs used in the present invention are fresh ginseng, white ginseng, hairy root ginseng, red ginseng, ginseng leaves of Panex ginseng, Panax quinquefolium, Panax notoginseng or Panax japonicus.

Examples of the herbal drugs used in the present invention are those which produce acidic nature such as Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon. At least one selected from the above group of herbal drugs can be used along with ginseng as a mixed prescription.

Among the above herbal drugs, Schizandrae Frutus contains various lignans and thus shows effects in prevention of hepatic damage, restoration of hepatic damage, normalization of hepatic functions, accelerating secretion of bile acid, and can be also used as an antibacterial agent, an antioxidant, a digestive, mainly associated with lungs, liver, and kidneys. Further, it also shows effects in release of fatigue, release of stress, release of eye fatigue, and improvement of cognitive capability.

Crataegi Fructus has effects of facilitation of secretion of gastric juice, antibacterial activity, and prolonged antihypertensive activity, and thus has been used as a stomachics as well as a preparation for intestinal disorders. Further, it also shows effects in expanding coronary arteries and lowering cholesterol level and thus has been used as an agent for improving blood circulation.

Corni Fructus is known to have effects such as diuresis, temporary release of hypertension, antibacterial activity, antihistamine activity, and is thus used as a nourishing tonic, an astringent and a hemostat.

*Citrus* junos is used as a spice while Aurantii fructus is an aromatic stomachics used as a material for food or herbal drugs. The fruits of both *Citrus* junos and Aurantii Fructus contain a large amount of plant organic acids and thus can be used as a substitute for vinegar or a spice to remove odors of fish.

Among the above herbal drugs, Mume Fructus has effects of antibacterial activity, facilitation of secretion of gastric juice, refreshment, and thirst quench, and is thus used as an astringent, an antitussive and expectorant, an antipyretics, and an anthelmintic.

Among the above herbal drugs, Chaenomelis Fructus helps body metabolism and facilitates the secretion of gastric juice.

Among the above herbal drugs, apples are abundant in vitamins and minerals, especially in fibers, and are thus effective as a preparation for intestinal disorders and a sedative.

Among the above herbal drugs, Fructus of Punica granatum has been known as a tonic and is effective in prevention of hypertension and arteriosclerosis. Further, it shows effects in treating diarrhea, dysentery, stomachache, leucorrhea and is also used as an anthelmintic.

*Citrus* limon contains a large amount of vitamin C and thus helps to release fatigue and maintain healthy skin.

As stated above, the present invention is characterized in that the ratio of ginsenoside (Rg3+Rg5)/(Rb1+Rb2+Rc+Rd) is much improved to 10-45 due to the synergy effect resulted by heat-extraction of the mixture consisting of ginseng and at least one herbal drugs selected from a group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon. Unlike the conventional extract of ginseng alone, the extract of the processed ginseng in the present invention exhibits superior pharmaceutical effects in treatment and prevention of hypertension, arteriosclerosis, thrombosis, erectile dysfunction, cerebral apoplexy, memory disorder, having an anticancer activity and alleviating side effects of anticancer agents.

In addition, the present invention also relates to a pharmaceutical drug or a healthy food comprising the extract of processed ginseng or its saponin fraction extract prepared according to the present invention, as an active ingredient and various pharmaceutical drugs, healthy foods and other food additives comprising the extract of the processed ginseng can be manufactured by a conventional formulation technologies. For example, the above pharmaceutical drugs can be prepared for oral administration in the form of tablets, hard capsules, soft capsules, pills, granules, liquid by using the conventional additives such as emulsifiers, lubricants, adhesives, sweeteners, aromatics, etc., as well as for injections.

Ginseng and herbal drugs, used in the present invention for preparation of the extract of the processed ginseng, have been used as a pharmaceutical drug or a dietary food, and heat treatment does not produce any harmful substances. Therefore, the extract of the processed ginseng or its saponin fraction extract can be safely taken.

It is preferable for adults to take 2-4 times daily, about 100-1,000 mg per one dose of the extract of the processed ginseng or its saponin fraction extract prepared according to the present invention.

When the extract of the processed ginseng or its saponin fraction extract is used as a food additive, they can be added to foods in the form of drinks, tablets, granules, pills, gums, and confectioneries.

As stated above, the processed ginseng extract can be administered in various forms of preparations and shows effects in improving erectile dysfunction, blood circulation, release of fatigue, hypertension, treatment of arteriosclerosis, treatment of thrombosis, treatment of cerebral apoplexy, improvement of brain functions, and also shows an anticancer activity and alleviate side effects of anticancer agents.

The following examples are intended to be illustrative of the present invention, however, they should not be construed as limiting the scope of this invention defined by the appended claims.

EXAMPLE 1

2.5 kg of white ginseng, 1.5 kg of Schizandrae Frutus and 40 L of water were mixed together in an extraction tank and boiled for 4 hr (the internal temperature is 120° C.). After removing 20 L of water by evaporation, the mixture was added with 48 L of ethanol, boiled for 2 hours, cooled down to room temperature and filtrated (First filtrate).

The residue was added with 18 L of water and 48 L of ethanol, heated to boil for 3 hours, cooled down and filtered (Second filtrate). The combined mixture of first and second filtrate was concentrated until it was reduced to one third in volume, spray-dried and a powder of the processed ginseng extract was finally obtained.

EXAMPLE 2

2.5 kg of white ginseng and 1.5 kg of Crataegii Fructus were processed same as in Example 1 and the resulting powder of the processed ginseng extract was obtained.

EXAMPLE 3

50 g of hairy root ginseng, 30 g of Schizandrae Frutus were mixed with 700 mL of water and boiled for 4 hours. The mixture was cooled down to room temperature and filtrated. The filtrate was then concentrated under vacuum and a processed ginseng extract was finally obtained.

EXAMPLE 4

20 g of red ginseng, 15 g of Schizandrae Frutus were mixed with 300 mL of water and boiled for 3 hours. The mixture was cooled down to room temperature and filtrated. The filtrate was then concentrated under vacuum and a processed ginseng extract was finally obtained.

EXAMPLE 5

25 g of minced fresh ginseng, 20 g of Crataegi Fructus were mixed with 200 mL of water and boiled for 4 hr. The mixture was cooled down to room temperature and filtrated. The filtrate was then concentrated under vacuum and a processed ginseng extract was finally obtained.

EXAMPLE 6

A processed ginseng extract was obtained by the process same as in Example 3 with 20 g of white ginseng, 25 g of Chaenomelis Fructus and 400 mL of water.

EXAMPLE 7

A processed ginseng extract was obtained by the process same as in Example 3 with 20 g of white ginseng, 15 g of fruit of Mume Fructus and 300 mL of water.

EXAMPLE 8

A processed ginseng extract was obtained by the process same as in Example 3 with 15 g of white ginseng, 15 g of fruit of *Citrus* junos and 200 mL of water.

EXAMPLE 9

A processed ginseng extract was obtained by the process same as in Example 3 with 15 g of red ginseng, 20 g of Aurantii Fructus and 300 mL of water.

EXAMPLE 10

20g of Panax Quinquefolium and 20g of Corni Fructus; 20g of Panax japonicus and 20g of Cartaegi Fructus; 15g of Panax notoginseng, 20g of dry ginseng leaves and 15g of Schizandrae Fructus were mixed with 350ml of water, respectively and boiled for 4 hours, thereafter the water was distilled off by evaporation. Then, the mixture was added with 400ml of ethanol and heated to reflux for 2 hours and cooled down to room temperature. The mixture was filtrated and the filtrate was concentrated under vacuum and a processed ginseng extract was finally obtained.

EXAMPLE 11

10 g of white ginseng and 10 g of Crataegi Fructus were mixed with 200 mL of water and boiled for 1 hour. After evaporating 100 mL of water, the remaining mixture was boiled for 3 hours and the remaining water was removed by evaporation. Then, the mixture was added with 400 mL of methanol and heated to reflux for 1 hour. The mixture was cooled down, filtrated and a processed ginseng extract was finally obtained.

EXAMPLE 12

10 g of white ginseng and 10 g of Schizandrae Fructus were processed same as in Example 11 and a processed ginseng extract was finally obtained.

EXAMPLE 13

10 g of white ginseng and 10 g of Corni Fructus were processed as same as in Example 11 and processed ginseng extract was finally obtained.

EXAMPLE 14

10 g of white ginseng and 10 g of Chaenomelius Fructus were processed same as in Example 11, and a processed ginseng extract was finally obtained.

EXAMPLE 15

10 g of white ginseng and 10 g of fruit of Mume Fructus were processed same as in Example 11, and a processed ginseng extract was finally obtained.

EXAMPLE 16

10 g of white ginseng and 10 g of fruit of *Citrus* junos were processed same as in Example 11, and a processed ginseng extract was finally obtained.

EXAMPLE 17

10 g of white ginseng and 10 g of Aurantii Fructus were processed same as in Example 11, and a processed ginseng extract was finally obtained.

EXAMPLE 18

10 g of red ginseng and 10 g of Schizandrae Fructus were processed same as in Example 11, and a processed ginseng extract was finally obtained.

EXAMPLE 19

50 g of the processed ginseng extract obtained from Example 1 was dissolved in 350 mL of water and then extracted two times with 350 mL of dichloromethane. The aqueous layer was extracted three times with 350 mL of water-saturated butanol and the extracts were combined together. Then the combined extract was washed with 350 mL of water. The butanol layer was concentrated under vacuum and a saponin fraction of the processed ginseng extract was finally obtained.

EXAMPLE 20

50 g of the processed ginseng extract obtained from Example 2 was dissolved in 350 mL of water and then extracted two times with 350 mL of dichloromethane. The aqueous layer was extracted three times with 350 mL of water-saturated butanol and the extracts were combined together. Then the combined extract was washed with 350 mL of water. The butanol layer was concentrated under vacuum and a saponin fraction of the processed ginseng extract was finally obtained.

EXAMPLE 21

5.1 g of the processed ginseng extract obtained from Example 11 was dissolved in 50 mL of water and then extracted two times with 50 mL of dichloromethane. The aqueous layer was extracted three times with 50 mL of water-saturated butanol and the extracts were combined together. Then the combined extract was washed with 50 mL of water. The butanol layer was concentrated under vacuum and a saponin fraction of the processed ginseng extract was finally obtained.

EXAMPLE 22

5.4 g of the processed ginseng extract obtained from Example 12 was processed same as in Example 21, and a saponin fraction of the processed ginseng extract was finally obtained.

EXAMPLE 23

5 g of the processed ginseng extract obtained from Example 13 was processed same as in Example 21, and a saponin fraction of the processed ginseng extract was finally obtained.

EXAMPLE 24

5.5 g of the processed ginseng extract obtained from Example 14 was processed same as in Example 21, and a saponin fraction of the processed ginseng extract was finally obtained.

EXAMPLE 25

4.8 g of the processed ginseng extract obtained from Example 15 was processed same as in Example 21, and a saponin fraction of the processed ginseng extract was finally obtained.

EXAMPLE 26

4.9 g of the processed ginseng extract obtained from Example 16 was processed same as in Example 21, and a saponin fraction of the processed ginseng extract was finally obtained.

EXAMPLE 27

5.1 g of the processed ginseng extract obtained from Example 17 was processed same as in Example 21, and a saponin fraction of the processed ginseng extract was finally obtained.

EXAMPLE 28

5.2 g of the processed ginseng extract obtained from Example 18 was processed same as in Example 21, and a saponin fraction of the processed ginseng extract was finally obtained.

EXAMPLE 29

15 g of white ginseng, 5 g of Crataegi Fructus and 5 g of Schizandrae Fructus were mixed with 250 mL of water and boiled for 5 hr. The mixture was cooled down to room temperature and filtrated. The filtrate was concentrated under vacuum and a processed ginseng extract was finally obtained.

EXAMPLE 30

15 g of white ginseng, 4 g of Corni Fructus, 3 g of Crataegi Fructus, and 3 g of Schizandrae Fructus were processed same as in Example 29, and a processed ginseng extract was finally obtained.

REFERENCE EXAMPLE 1

Preparation of Tablets 500 g of the processed ginseng extract powder obtained from Example 1, 196 g of crystalline cellulose and 4 g of magnesium stearate were mixed thoroughly and 700 mg tablets were manufactured according to a conventional tableting method.

REFERENCE EXAMPLE 2

Preparation of Tablets 500 g of the processed ginseng extract powder obtained from Example 2, 196 g of crystalline cellulose and 4 g of magnesium stearate were mixed thoroughly and 700 mg tablets were manufactured according to a conventional tableting method.

REFERENCE EXAMPLE 3

Preparation of Hard Capsules 100 g of the processed ginseng extract powder obtained from Example 1, 95 g of crystalline cellulose and 5 g of silicon dioxide($SiO_2$) were mixed thoroughly and 400 mg hard capsules were manufactured according to a conventional method.

REFERENCE EXAMPLE 4

Preparation of Soft Capsules 200 g of the processed ginseng extract powder obtained from Example 1, 280 g of soybean oil, 15 g of lecithin and 5 g of yellow wax were mixed thoroughly and 500 mg soft capsules were manufactured according to a conventional method.

REFERENCE EXAMPLE 5

Preparation of Granules 500 g of the processed ginseng extract powder obtained from Example 2, 196 g of corn starch, 4 g of magnesium stearate were mixed thoroughly and granules were manufactured according to a conventional method.

REFERENCE EXAMPLE 6

Preparation of Pills 300 g of the processed ginseng extract powder obtained from Example 2, 100 g of corn starch, 50 g of crystalline cellulose and 150 g of honey were mixed thoroughly and 100 mg pills were manufactured according to a conventional method.

REFERENCE EXAMPLE 7

Preparation of Liquids 100 g of the processed ginseng extract powder obtained from Example 1, 20 g of concentrated red ginseng extract (ginseng saponin 140 mg/g), 100 g of powder extract of Cordyceps, 50 g of Zizyphi Fructus concentrate (brix 55), 2 g of vitamin B1 hydrochloride, 1 g of vitamin B2, 2 g of vitamin B6 hydrochloride, 200 g of sugar were dissolved in purified water to the final volume of 2 L and liquid preparations were finally manufactured.

REFERENCE EXAMPLE 8

Preparation of Drinks 10 g of the processed ginseng extract powder obtained from Example 1, 1 g of citric acid, 1 g of gum arabic, 5 g of sugar were dissolved in purified water to the final volume of 100 mL. The above mixture was sterilized for 15 seconds at 95° C. and cooled down and drinks were finally manufactured.

COMPARATIVE EXAMPLE 1

A powder of extract was obtained by the process same as in Example 3 by using 2 kg of red ginseng, 5 kg of white ginseng, 5 kg of Schizandrae Fructus and 5 kg of Crataegi Fructus, respectively.

COMPARATIVE EXAMPLE 2

10 g of white ginseng was mixed with 200 mL of water and boiled for 1 hr. After evaporating 100 mL of water, the mixture was boiled for 3 hours and the remaining water was removed by distillation. Then, the mixture was added with 400 mL of methanol and heated to reflux for 1 hour, cooled down, filtrated and a processed ginseng extract was finally obtained.

COMPARATIVE EXAMPLE 3

10 g of red ginseng was processed same as in Comparative Example 2, and red ginseng extract was finally obtained.

COMPARATIVE EXAMPLE 4

3.4 g of the processed ginseng extract obtained from Comparative Example 2 was dissolved in 50 mL of water and then extracted two times with 50 mL of dichloromethane. The aqueous layer was extracted three times with 50 mL of water-saturated butanol three times and the extracts were combined together. Then the combined extract was washed with 50 mL of water. The butanol layer was concentrated under vacuum and a saponin fraction of the processed ginseng extract was finally obtained.

COMPARATIVE EXAMPLE 5

3.4 g of red ginseng extract obtained from Comparative Example 3 was processed same as in Comparative Example 4, and a saponin fraction of the processed ginseng extract was finally obtained.

COMPARATIVE EXAMPLE 6

Preparation of Sun Ginseng (Korean Pat. No. 192678)

A 40 mL stainless container added with 5 g of white ginseng and 5 mL of water was placed into an autoclave and heated for 2 hours at 120° C. 5 g of the processed ginseng was collected and then extracted 3 times with 100 mL of methanol, respectively. The extract was concentrated, suspended in water and then extracted 3 times using 100 mL of ether, respectively. The residual aqueous phase was extracted 3 times with 100 mL of butanol, respectively. The butanol fraction was concentrated and a saponin fraction of sun ginseng extract was finally obtained.

COMPARATIVE EXAMPLE 7

Preparation of Sun Ginseng (Korean Pat. No. 192678)

A 40 mL stainless container added with 5 g of white ginseng and 5 mL of water was placed into an autoclave and heated for 2 hours at 130° C. 5 g of the processed ginseng was collected and then extracted 3 times with 100 mL of methanol, respectively. The extract was concentrated, suspended in water and then extracted 3 times using 100 mL of ethyl ether, respectively. The residual aqueous phase was extracted 3 times with 100 mL of butanol, respectively. The butanol fraction was concentrated and a saponin fraction of sun ginseng extract was finally obtained.

COMPARATIVE EXAMPLE 8

5 g of red ginseng was extracted 3 times by heating to reflux for 3 hours with 100 mL of methanol, respectively. The extract was concentrated, suspended in water and then extracted 3 times with 100 mL of ethyl ether, respectively. The aqueous phase was extracted 3 times with 100 mL of butanol, respectively. The extracts were combined, concentrated and a saponin fraction of red ginseng extract was finally obtained.

REFERENCE COMPARATIVE EXAMPLE 1

350 g of white ginseng extract powder, 210 g of Schizandrae Fructus extract obtained from Comparative Example 1, 136 g of crystalline cellulose and 4 g of magnesium stearate were mixed thoroughly and 700 mg tablets were manufactured according to a conventional tableting method.

REFERENCE COMPARATIVE EXAMPLE 2

350 g of white ginseng extract powder, 210 g of Crataegi Fructus extract obtained from Comparative Example 1, 136 g of crystalline cellulose and 4 g of magnesium stearate were mixed thoroughly and 700 mg tablets were manufactured according to a conventional tableting method.

REFERENCE COMPARATIVE EXAMPLE 3

350 g of red ginseng extract powder obtained from Comparative Example 1, 246 g of crystalline cellulose, 100 g of corn starch and 4 g of magnesium stearate were mixed thoroughly and 700 mg tablets were manufactured according to a conventional tableting method.

EXPERIMENTAL EXAMPLE 1

Figure 2:
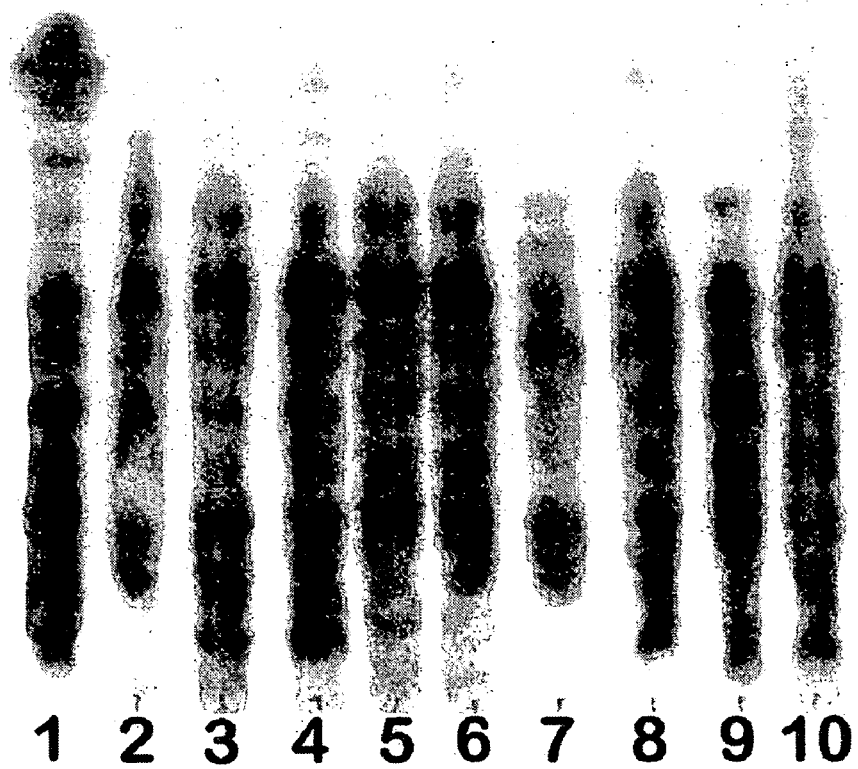
FIG. 2 shows a thin layer chromatogram of saponin fraction of the processed ginseng of the present invention and saponin fraction of the conventional ginseng (1: Comp. Ex. 4; 2: Ex. 22; 3: Ex. 21; 4: Ex. 23; 5: Ex. 24; 6: Ex. 25; 7: Ex. 26; 8: Ex. 27; 9: Comp. Ex. 5; 10: Ex. 28)

The saponin fraction extract obtained from Examples 21-28 and Comparative Examples 4-5 were analyzed by thin layer chromatography (a developing solvent; chloroform:methanol:water=15:10:2.5/a color developer; heat after spray with 10% sulfuric acid) (FIGS. 1 and 2). High Performance Liquid Chromatograpy(HPLC) was performed using Capcell pak MG C18(4.6×250 mm), detection at 203 nm. The separation was carried out by gradient elution, using solvents (A)10% acetonitrile/water and (B)90% acetonitrile/water and the result is shown in FIG. 3.

As shown in FIGS. 1 and 2, there was no change in ginsenosides in Comparative Examples 4 and 5. However, most ginsenosides changed into those having less polarities in Examples 21-28.

Figure 3:
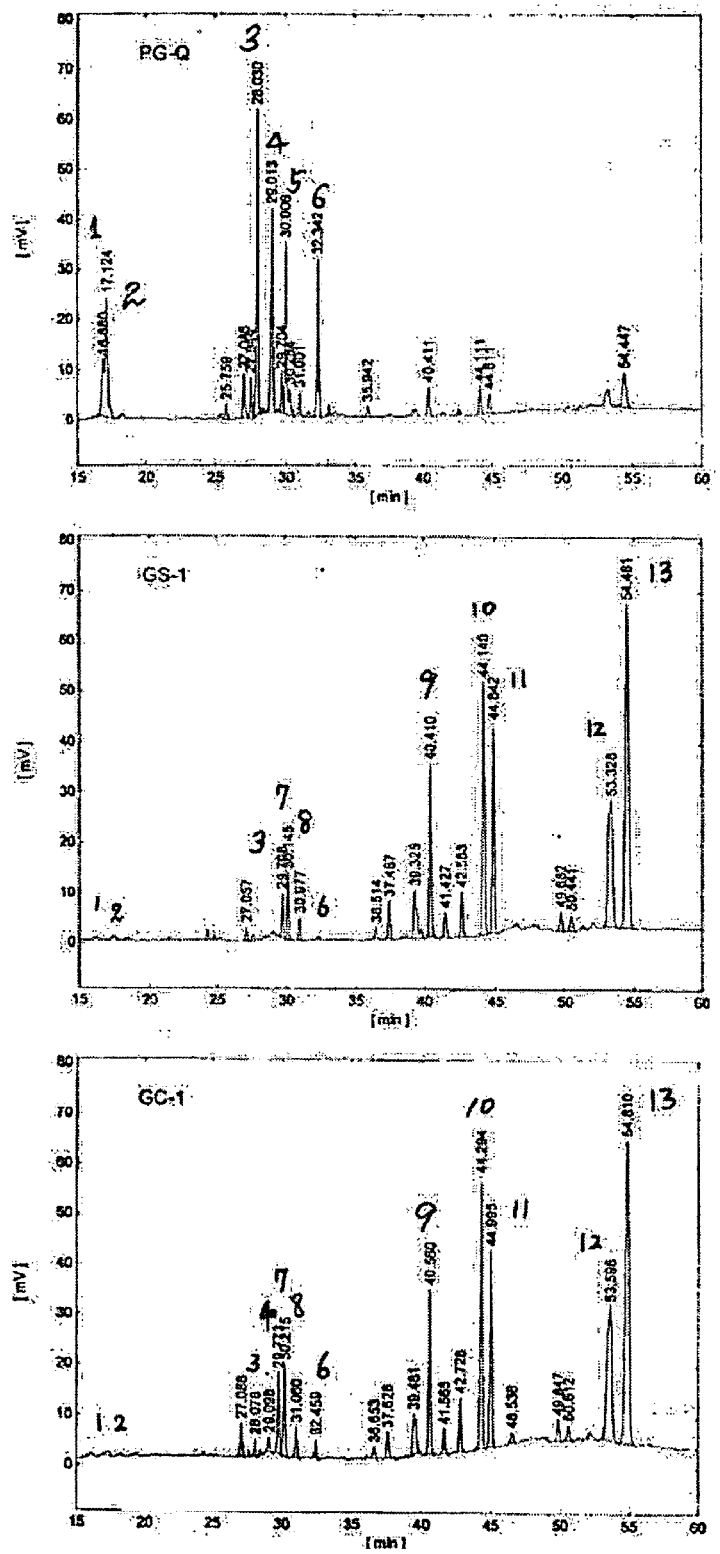
FIG. 3 shows results of high performance liquid chromatography of saponin fraction of the ginseng processed by white ginseng plus Schizandrae Fructus or white ginseng plus Crataegi Fructus(PG-Q: Comp. Ex. 4; GC-1: Ex. 21; GS-1: Ex. 22)

As shown in FIG. 3, most ginsenosides in Comparative Example 4(indicated as PG-Q) changed into Rg3, Rg5, Rk1, Rg2, Rh1, and F4 in Examples 21 and 22 (GS-1: Example 22, GC-1: Example 21). Peaks 1, 2, 3, 4, 5, 6, 7, 8, 9, 10, 11, 12, 13 represents Rg1, Re, Rb1, Rc, Rb2, Rd, Rg2, Rh1, F4, (20S)-Rg3, (20R)-Rg3, Rk1, Rg5, respectively.

The saponin fraction extract obtained form Examples 19-28 and Comparative Examples 4-7 were analyzed by HPLC and the ratio of ginsenoside (Rg3+Rg5)/(Rb1+Rb2+Rc+Rd) was analyzed according to the relative area of peak for each component and the result is shown in the following Table 1.

TABLE 1

Comparison of Relative Area of Peaks for Saponin Fraction Extract

| Sample | Rg3 | Rg5 | Rb1 | Rb2 | Rc | Rd | (Rg3 + Rg5)/(Rb1 + Rb2 + Rc + Rd) |
|---|---|---|---|---|---|---|---|
| Ex. 19 | 27.35 | 29.90 | 0.12 | 1.01 | 0.14 | 0.11 | 41.48 |
| Ex. 20 | 28.84 | 31.31 | 0.10 | 1.20 | 0.17 | 0.10 | 38.31 |
| Ex. 21 | 24.40 | 26.43 | 0.61 | 0.71 | 2.27 | 0.61 | 12.10 |
| Ex. 22 | 25.63 | 28.63 | 0.22 | 1.61 | 0.30 | 0.20 | 23.28 |
| Ex. 23 | 26.12 | 28.94 | 0.28 | 1.48 | 0.40 | 0.34 | 22.02 |
| Ex. 24 | 27.63 | 29.80 | 1.22 | 1.50 | 1.54 | 1047 | 10.02 |
| Ex. 25 | 24.32 | 27.36 | 0.52 | 0.64 | 2.15 | 0.52 | 13.49 |
| Ex. 26 | 25.84 | 28.64 | 0.24 | 1.12 | 0.34 | 0.28 | 27.51 |
| Ex. 27 | 24.77 | 27.04 | 0.31 | 1.00 | 0.83 | 0.41 | 20.31 |
| Ex. 28 | 26.44 | 29.20 | 0.20 | 0.74 | 0.22 | 0.28 | 38.63 |
| Comp. Ex. 4 | 3.82 | 4.42 | 19.22 | 11.17 | 17.09 | 10.55 | 0.14 |
| Comp. Ex. 6 | 24.12 | 11.35 | 10.46 | 7.74 | 10.66 | 5.58 | 1.03 |
| Comp. Ex. 7 | 21.00 | 16.17 | 4.06 | 3.44 | 3.98 | 3.82 | 2.43 |
| Comp. Ex. 8 | 1.05 | 1.05 | 30.11 | 9.69 | 12.45 | 1.76 | 0.03 |

As shown in the above Table 1, the ratio of ginsenoside (Rg3+Rg5)/(Rb1+Rb2+Rc+Rd) of the processed ginseng extract prepared according to the present invention ranged 10-45 thus being much superior to those obtained in Comparative Examples 6 and 7, wherein the ratio ranged 1.03-2.43. Further, although the processed ginseng saponins prepared in Examples 19 and 20 are obtained by using the same herbal drugs as in Examples 21 and 22, the ratio of ginsenoside (Rg3+Rg5)/(Rb1+Rb2+Rc+Rd) of the processed ginseng saponins prepared in Examples 19 and 20 was much increased even though in a larger scale due to bulk process as compared to those obtained in Examples 21 and 22.

EXPERIMENTAL EXAMPLE 2

Effect of Improving Erectile Dysfunction

Forty males aged 45-60 with erectile dysfunction were divided into 5 groups so that each group consists of 8 males. They were administered for 30 days with 2 tablets per each administration, 3 times daily, prepared in the above Reference Examples 1 and 2, Reference Comparative Examples 1, 2 and 3. The effects of the administration are shown in Table 2.

TABLE 2

Effects of Processed Ginseng Extract on Improvement of Erectile Dysfunction

| Classification | Ref. Ex. 1 | Ref. Ex. 2 | Ref. Comp. Ex. 1 | Ref. Comp. Ex. 2 | Ref. Comp. Ex. 3 |
|---|---|---|---|---|---|
| Marked Improvement | 4 males | 4 males | 0 male | 0 male | 1 male |
| Improvement | 2 males | 2 males | 1 male | 1 male | 2 males |
| Little Improvement | 1 male | 1 male | 1 male | 1 male | 1 male |
| No Change | 1 male | 1 male | 6 males | 6 males | 4 males |
| Total No. of Subjects | 8 males | 8 males | 8 males | 8 males | 8 males |
| Effective Rate (%) | 87.5 | 87.5 | 25 | 25 | 50 |

As shown in Table 2, the males administered with the processed ginseng extract obtained according to the present invention as in the Reference Examples 1 and 2 showed 87.5% of improvement of erectile dysfunction while those in the Reference Comparative Examples 1 and 2 showed no significant effect. It has been also known that red ginseng extract (Reference Comparative Example 3) has a therapeutic effect to improve erectile dysfunction, however, the processed ginseng extract prepared according to the present invention showed a superior effect on improving erectile dysfunction to conventional ginseng extract.

EXPERIMENTAL EXAMPLE 3

Effect of Improving Peripheral Blood Circulation

Forty diabetic males aged 45-60 with a minor neural disorder were divided into 5 groups so that each group consists of 8 males. They were administered with 6 tablets prepared in the above Reference Examples 1 and 2, Reference Comparative Examples 1 and 2, and blood flow of the right foot of each subject was measured before administration, 45 and 90 minutes after administration, respectively, using Laser Doppler Flowmetry. Placebo group was administered with tablets prepared by using the same amount of corn starch. The effects of the administration are shown in Table 3.

TABLE 3

Effects of Processed Ginseng Extract on Improvement of Blood Circulation (Unit: Blood Flow mL/min/100 g tissue)

| Classification | Before Administration | 45 min After Administration | 90 min After Administration |
|---|---|---|---|
| Ref. Ex. 1 | 4.1 ± 1.5 | 5.5 ± 1.8 | 6.2 ± 2.0 |
| Ref. Ex. 2 | 4.1 ± 1.4 | 5.8 ± 1.7 | 6.9 ± 1.9 |
| Ref. Comp. Ex. 1 | 4.0 ± 1.6 | 4.2 ± 1.5 | 4.6 ± 1.6 |
| Ref. Comp. Ex. 2 | 4.2 ± 1.6 | 4.5 ± 1.6 | 5.0 ± 1.7 |
| Placebo Group | 4.2 ± 1.5 | 4.1 ± 1.4 | 4.3 ± 1.6 |

As shown in Table 3, there was significant increase of blood circulation of 51.2% and 68.2%, respectively, in subjects in Reference Examples 1 and 2 while the increase of blood circulation in the group of Reference Comparative Examples 1 and 2 were only 15% and 19%, respectively, thus showing the superior effect of the processed ginseng extract prepared according to the present invention in promoting blood circulation.

EXPERIMENTAL EXAMPLE 4

Comparison of Vasorelaxation Effect

The thoracic aorta was isolated from Sprague-Dawley rats and cut into rings of 2-3 mm width with extreme care to preserve endothelium intact. The aortic preparations were suspended between wire hooks in an organ bath containing 20 ml of Krebs' bicarbonate buffer (mM: NaCl, 118; KCl 4.7; $CaCl_2$, 2.5; $NaHCO_3$, 25; $MgSO_4$, 1.2; $KH_2PO_4$, 1.2; and glucose, 11.0) bubbled with mixture gas (95% $O_2$, 5% $CO_2$) and maintained at 37° C. The aortic preparations were allowed to equilibrate for 60 minutes under the resting tension of 2 grams. The isometric contractile response was measured with a force displacement transducer (Grass FT03, Grass Ins., Quincy, Mass., USA) and displayed on a chart recorder (Multicorder MC 6625, Hugo Sachs Electronic, March, Germany). The aortic preparations were precontracted submaximally with phenylephrine (PE, 300 nM). After the contraction was stabilized, acetylcholine (1 μM) was added to confirm the presence of the endothelium. Then, the aortic preparations were washed out 3 times for 45 min, and rechallenged with PE. After PE, response reached the plateau, all compounds (1 μM-1 mM) were cumulatively added to the tissue bath. The samples used were saponin fraction extract obtained in Examples 21 and 22 and Comparative Example 4.

Figure 4:
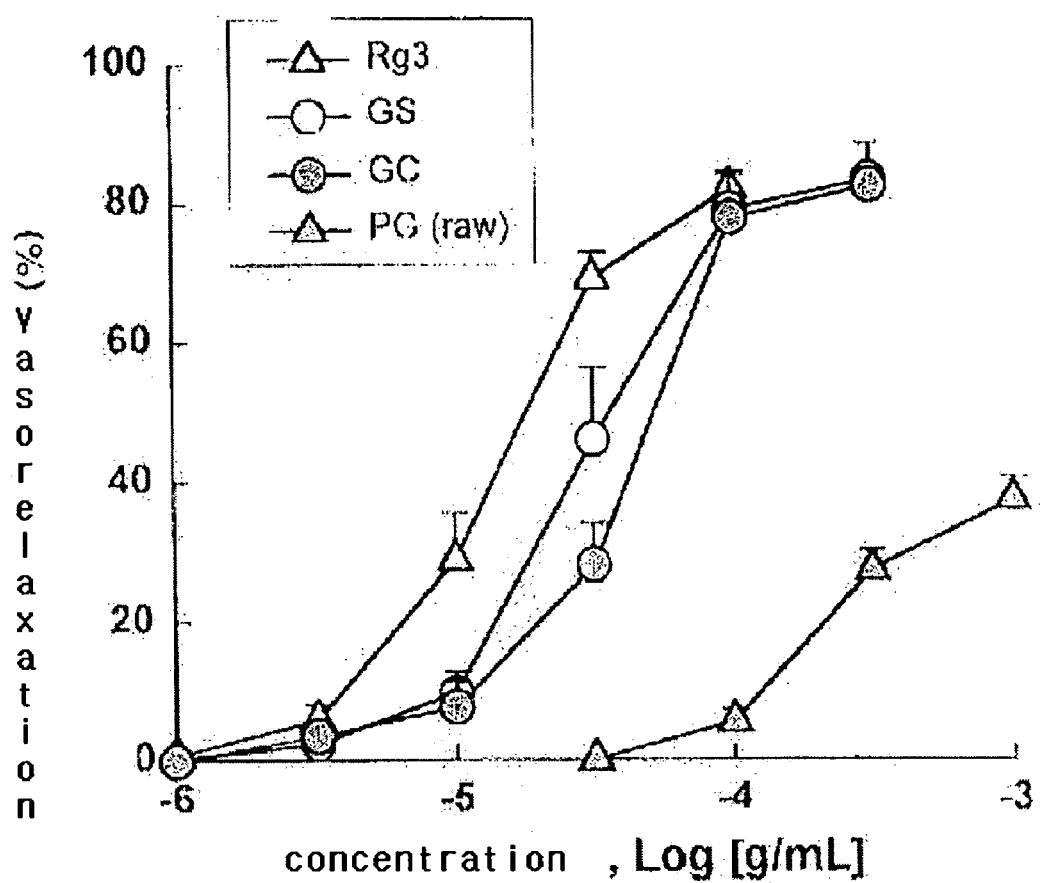
FIG. 4 shows the comparative results of relaxation of blood vessels by saponin fraction of the processed ginseng according to the present invention, of saponin fraction of the conventional ginseng and ginsenoside Rg3.

As shown in FIG. 4, the vasorelaxation effect of the saponin fraction extract of the processed ginseng according to the present invention was superior to that of Comparative Example 4. For example, the vasorelaxation effect of the saponin fraction extracts of the processed ginseng obtained in Example 21 (represented by dark circle) and Example 22 (represented by blank circle) was greater than that of the saponin fraction extract of Comparative Example 4(represented by dark triangle) by 65 times and 97 times, respectively. The processed ginseng prepared according to the present invention showed superior pharmaceutical effects to the processed ginseng disclosed in Korean Pat. No. 192678 and J. of Natural Products 63, 1702, 2000.

EXPERIMENTAL EXAMPLE 5

Effect on Hypertension

Twenty one males aged 45-60 with hypertension were divided into 2 groups of 10 males and 11 males. One group was administered for 30 days with 2 tablets per each administration, 3 times daily, prepared in Reference Example 2 while the other group was administered with those prepared in Reference Comparative Example 2, and blood pressure were measured. The results of the measurements of the blood pressure are shown in Table 4.

TABLE 4

Hypotensive Effect of the processed ginseng

| Patient | Ref. Ex. 2 (Bef. Adm. -> After Adm.) (mmHg) | Change (mmHg) | Patient | Ref. Comp. Ex. 2 (Bef. Adm. -> After Adm.) (mmHg) | Change (mmHg) |
|---|---|---|---|---|---|
| 1 | 148 -> 120 | −28 | 12 | 160 -> 162 | +2 |
| 2 | 150 -> 128 | −22 | 13 | 170 -> 170 | 0 |

TABLE 4-continued

Hypotensive Effect of the processed ginseng

| Patient | Ref. Ex. 2 (Bef. Adm. -> After Adm.) (mmHg) | Change (mmHg) | Patient | Ref. Comp. Ex. 2 (Bef. Adm. -> After Adm.) (mmHg) | Change (mmHg) |
| --- | --- | --- | --- | --- | --- |
| 3 | 178 -> 150 | −28 | 14 | 166 -> 164 | −2 |
| 4 | 160 -> 146 | −14 | 15 | 158 -> 143 | −15 |
| 5 | 162 -> 130 | −32 | 16 | 156 -> 154 | −2 |
| 6 | 154 -> 126 | −28 | 17 | 150 -> 148 | −2 |
| 7 | 158 -> 130 | −28 | 18 | 160 -> 143 | −17 |
| 8 | 166 -> 146 | −20 | 19 | 172 -> 170 | −2 |
| 9 | 180 -> 144 | −36 | 20 | 160 -> 164 | +4 |
| 10 | 170 -> 168 | −2 | 21 | 154 -> 160 | +6 |
| 11 | 158 -> 140 | −18 | | | |

As shown in Table 4, the processed ginseng extract according to the present invention reduced the systolic blood pressure of patients with hypertension by 90.9% when they were administered for one month and the resulting blood pressure decrease was −14~−36 mmHg, whereas the patients administered with the mixture of Craetagi fructus extract and the conventional ginseng extract showed that only 20% were reduced in blood pressure while there was no observable changes for the remaining 80%, thus showing the superiority of the processed ginseng extract of the present invention in reducing the systolic blood pressure.

EXPERIMENTAL EXAMPLE 6

Effect of Anti-Platelet Aggregation

Blood collected from branchial vein of a healthy male (15% citric aicd-citrate-dextrose was used as an anticoagulant) was centrifuged for 15 min at 120×g to separate blood plasma. Thus obtained blood plasma was centrifuged for 10 minutes at 500×g to obtain platelets. The platelets were suspended to 200 million platelets/mL to obtain washed platelets. The effects of the processed ginseng extract on the platelet aggregation induced by collagens were measured in accordance with the method in Journal of Ginseng Research (vol. 21, 132, 1997) and the results are shown in Table 5.

TABLE 5

Inhibitory effect of processed ginseng extract against platelet aggregation induced by collagens

| Classification | $IC_{50}$ (µg/mL) |
| --- | --- |
| Example 21 | 11.5 ± 1.2 |
| Example 22 | 9.4 ± 1.4 |
| Comparative Example 4 | 492.0 ± 14.4 |

As shown in Table 5, where 50% inhibitory concentrations ($IC_{50}$) were compared, the processed ginseng extract of the present invention showed 52 times and 42 times greater potency, respectively, than that of the conventional ginseng extract (Comparative Example 4) in the inhibitory effects against platelet aggregation, thus being expected as a strong candidate for the treatment of hypertension, arteriosclerosis, cerebral apoplexy and the like.

EXPERIMENTAL EXAMPLE 7

Effect on Alleviating Side Effects of Anti-Cancer Agents

The effect of the saponin fraction of the processed ginseng of the present invention on alleviating side effects resulted from administration of cisplatin, an anti-cancer agent, especially on reduced renal function, was measured. Thirty Sprag Dowry rat weighing about 200 g were divided into five groups so that each group consists of six mice and were intraperitoneally injected with 5 mg/kg/mL of cisplatin solution except the control group, which was injected with saline solution. 300 mg/kg of saponin fraction extracts obtained in Example 22 and Comparative Example 4, respectively, were intraperitoneally injected 72, 48, 24, 12 hours prior to cisplatin administration (group of pre-treatment), and also intraperitoneally injected 12, 24, 48, 72 hours after cisplatin injection (group of post-treatment). On the fourth day, blood was collected form the mice and blood sera were prepared.

Blood nitrogen urea(BUN), a renal toxic index, was measured using BUN measuring kit. 0.02 mL of a mixture consisting of 0.1 mL of original concentrate of urease and 20 mL of buffer solution was added with blood sera prepared from the blood of the above mice and 0.02 mL of urea standard solution, incubated for 15 minutes at 37° C. and added with 2 mL of a developing reagent, incubated for 5 minutes at 37° C. and optical density was measured at 570 nm.

Creatinine, a renal toxic index, was measured using a creatinine measuring kit.

0.5 mL of blood sera prepared from the above mice was added with 4 mL of tungstate solution, vigorously stirred and then centrifuged for 10 minutes at 1500×g. The supernatant was recovered and mixed with 3 mL of creatine standard (control group was added with 3 mL of distilled water), 1 mL of picrate solution and 0.5 mL of 1.4 M NaOH solution and mixed well. After 15 minutes, optical density was measured at 515 nm.

TABLE 6

Effect of saponin fraction extract on improving renal toxicity resulted from anti-cancer agent

| Classification | BUN (mg/dL) | Creatinine (mg/dL) |
| --- | --- | --- |
| Control group | 21.1 ± 2.3 | 0.51 ± 0.14 |
| Group treated with cisplatin | 98.5 ± 2.5 | 3.45 ± 0.40 |
| Group pre-treated with Ex. 22 | 75.4 ± 2.4 | 1.58 ± 0.20 |
| Group post-treated with Ex. 22 | 20.5 ± 2.6 | 0.64 ± 0.18 |
| Group post-treated with Comp. Ex. 4 | 78.6 ± 2.4 | 2.48 ± 0.31 |

As shown in Table 6, the group post-treated with saponin fraction extract obtained in Example 22 showed that the values of BUN and creatinine were recovered close to normal state.

EXPERIMENTAL EXAMPLE 8

Measurement of Protective Effects of Cerebral Neurons

In order to investigate the effect of saponin fraction extract of the processed ginseng of the present invention on the treatment and prevention of cerebral apoplexy, the effect of saponin fraction extract on the death of cerebral neurons due to overexposure of glutamate was measured in accordance with the method in J. Neurosci. Res. 53, 426 (1998) and the results are shown in Table 7.

TABLE 7

Protective effect of saponin fraction extract against the death of cerebral neurons due to overexposure of glutamate

| Classification | Concentration (μg/mL) | Cell Vitality (%) |
|---|---|---|
| Control group | — | 100 |
| Group treated with glutamate | — | 0 |
| Example 20 | 0.008 | 48.4 ± 3.8 |
|  | 0.08 | 72.8 ± 2.8 |
|  | 0.8 | 45.2 ± 5.1 |
| Comparative Example 4 | 0.05 | 30.4 ± 3.6 |
|  | 0.5 | 46.8 ± 3.4 |
|  | 5.0 | 70.6 ± 2.8 |
|  | 50.0 | 30.5 ± 2.7 |

As shown in Table 7, the saponin fraction extract obtained in Example 20 showed superior preventive effect to that in Comparative Example 4 against neural toxicity due to glutamate.

EXPERIMENTAL EXAMPLE 9

Antitumor Activity

Human cancer cells were inoculated in bovine calf serum culture media and cultured for 48 hours and then subcultured for one day in a 96-well culture. Forty eight hours after treating with the processed ginseng extract, the culture was added with MTT solution and formed insoluble formazine. After centrifugation, the precipitate was added with dimethylsulfoxide to dissolve the formazine and optical density was measured at 570 nm using an automatic flat reader. The concentration at which 50% of cells survive was calculated and the result is shown in table 8.

TABLE 8

Inhibitory activity of saponin fraction extract of the processed ginseng on growth of human cancer cells (MTT assay)

| Classification | SK-Hep-1 | Chang Liver | HeLa |
|---|---|---|---|
| Ex. 21 | 8.9 | 16.8 | 7.2 |
| Ex. 22 | 8.1 | 14.4 | 6.6 |
| Comp. Ex. 4 | 65.8 | 115.6 | 64.5 |

Unit: 50% inhibitory concentration ($IC_{50}$: μg/mL)

As shown in Table 8, the saponin fraction of the processed ginseng of the present invention (Examples 21 and 22) showed much stronger antitumor activity compared to that of conventional extract of white ginseng (Comparative Example 4).

Further, antitumor activity of saponin fraction was measured in accordance with the SRB(sulforhodamine B) assay and the result is shown in Table 8-1.

TABLE 8-1

In vitro Antitumor Activity (unit: 50% effective concentration (μg/mL))

| Sample | Cancer cells | | | | |
|---|---|---|---|---|---|
|  | A549 | Sk-OV-3 | SK-MEL-2 | XF498 | HCT15 |
| Ex. 21 | 43.4 | 31.2 | 16.5 | 23.4 | 40.4 |
| Ex. 22 | 23.7 | 28.9 | 16.1 | 19.2 | 22.2 |
| Comp. Ex. 4 | >100.0 | >100.0 | >100.0 | >100.0 | >100.0 |

As shown in Table 8-1, the saponin fraction of the processed ginseng of the present invention (Examples 21 and 22) showed much stronger antitumor activity compared to that of conventional extract of white ginseng (Comparative Example 4).

EXPERIMENTAL EXAMPLE 10

Comparison of Improvement in Cerebral Functions

Twenty senile people aged 61-70 with memory loss disorder (10 males and 10 females) were divided into 2 groups having equal number of males and females in each group and administered with 2 tablets per each administration two times daily for 3 months, prepared in Reference Example 2, Reference comparative Example 2, respectively. The degree of memory improvements was observed by questionnaires and the result is shown in Table 9.

In Table 9, when combining 'improved' and 'remarkably improved' being considered as effective ones, the processed ginseng extract of the present invention in Reference Example 2 showed 80% of an effective rate as compared to 30% of the conventional ginseng extract, thus showing the superiority of the processed ginseng extract of the present invention in improving cerebral functions via improving memory loss disorder.

TABLE 9

Level of Improvement in Cerebral functions

| Classification | Reference Example 2 (No. of people) | Reference Comparative Example 2 (No. of people) |
|---|---|---|
| Remarkably Improved | 5 | 1 |
| Improved | 3 | 2 |
| Negligible | 2 | 7 |
| Total | 10 | 10 |

EXPERIMENTAL EXAMPLE 11

Toxicity Test

Toxicity test of the processed ginseng extract was performed as follows. The processed ginseng extracts obtained in Examples 1 and 2 were dissolved in 0.2% Tween 80 solution and 5 g of the extract per kg body weight was orally administered to ICR mice (20 mice per group) with body weight of about 20 g. The mice were observed for 7 days and no death were observed.

INDUSTRIAL APPLICABILITY

As described above, the method employed in the present invention, wherein ginseng is mixed with at least one herbal drug(s) selected from the group consisting of such as Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus* limon, and boiled in water, can generate more potent synergistic pharmaceutical effects as compared to those of ginseng extract alone or those where ginseng extract and one or more herbal drugs are simply mixed after they are independently processed. This is because ginsenosides such as Rg3, Rg5, Rk1 and the like, which are not contained in white ginseng and contained in small amount in red ginseng, are contained in large amount in the processed ginseng extract prepared in the present invention, wherein the ratio of ginsenoside (Rg3+Rg5)/(Rb1+Rb2+Rc+Rd) is 10-45. The processed ginseng extract prepared in the present invention shows applicability as preventing and treating agent for improving erectile dysfunction, blood circulation, release of fatigue, hypertension, arteriosclerosis, thrombosis, cerebral functions, cerebral apoplexy, and an adjuvant therapeutic for cancer as a health supplementary food or a pharmaceutical drug. The processed ginseng extract prepared in the present invention can be manufactured and administered conveniently in forms such as liquids, tablets, granules, pills, hard capsules, or soft capsules.

What is claimed is:

1. A method of processing ginseng by heat-extraction, consisting of:
    (i) adding 4-10 times weight of water to a mixture consisting of 100 parts of ginseng and 10-1000 parts of at least one herbal drug selected from the group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *citrus limon*, and heating for 1-6 hours at 70-120° C. to form a heated mixture;
    (ii) cooling said heated mixture of part (i) to room temperature and filtering said mixture to form a filtrate; and
    (iii) concentrating said filtrate of part (ii) to form an extract or powder.

2. The method of claim 1, wherein said heating in step (i) is effected for 3-5 hours.

3. A method of processing ginseng by heat-extraction, consisting of:
    (i) adding 4-10 times weight of water to a mixture consisting of 100 parts of ginseng and 10-1000 parts of at least one herbal drug selected from the group consisting of Schizandrae Fructus, Crataegi Fructus, Corni Fructus, Chaenomelis Fructus, Mume Fructus, *Citrus* junos, Aurantii Fructus, apples, Fructus of *Punica granatum* and *Citrus limon*, and heating for 1-6 hours at 70-120° C. to form a heated mixture;
    (ii) evaporating the water in the heated mixture of part (i) to obtain a remaining mixture, and heating said remaining mixture for 1-3 hours in the presence of ethanol or methanol to produce a second heated mixture;
    (iii) cooling the second heated mixture of part (ii) to room temperature and filtering to form a filtrate; and
    (iv) concentrating said filtrate of part (iii) to form an extract or powder.

4. The method of claim 1, wherein said ginseng is selected from the group consisting of white ginseng, fresh ginseng, hairy root ginseng, red ginseng, ginseng leaves of *Panax ginseng, Panax quinquefolium, Panax notoginseng* and *Panax japonicus*.

5. The method of claim 3, wherein said ginseng is selected from the group consisting of white ginseng, fresh ginseng, hairy root ginseng, red ginseng, ginseng leaves of *Panax ginseng, Panax quinquefolium, Panax notoginseng* and *Panax japonicus*.

6. The method of claim 1, wherein said heating in said step (i) is effected for 3-5 hours.

* * * * *